(12) United States Patent
Hoogstraten

(10) Patent No.: US 6,414,226 B1
(45) Date of Patent: Jul. 2, 2002

(54) INBRED TOMATO LINE FDR 16-2045

(75) Inventor: Jaap Hoogstraten, Wageningen (NL)

(73) Assignee: Seminis Vegetable Seeds, Inc., Woodland, CA (US)

( * ) Notice: Subject to any disclaimer, the term of this patent is extended or adjusted under 35 U.S.C. 154(b) by 0 days.

(21) Appl. No.: 09/518,544

(22) Filed: Mar. 3, 2000

(51) Int. Cl.$^7$ .................................................. A01H 5/00

(52) U.S. Cl. ..................... 800/317.4; 800/298; 800/317

(58) Field of Search ...................... Plt./261; 800/317.4

(56) References Cited

PUBLICATIONS

De Franca et al, Tomato Breeding Program for Yield and Quality at Brazilian Northeast, 1994, ISHS, Wageningen (Netherlands) Acta Horticulturae 376, pp. 81–83.*

* cited by examiner

Primary Examiner—Bruce R. Campbell
Assistant Examiner—June Hwu
(74) Attorney, Agent, or Firm—Rothwell, Figg, Ernst & Manbeck

(57) ABSTRACT

The present invention relates to a new and distinct inbred tomato line, designated FDR 16-2045. This invention also relates to plants and seeds of inbred tomato line FDR 16-2045 and methods for producing a tomato plant produced by crossing the inbred line FDR 16-2045 with itself or another tomato plant.

29 Claims, No Drawings

US 6,414,226 B1

INBRED TOMATO LINE FDR 16-2045

TECHNICAL FIELD OF THE INVENTION

The present invention relates to a new and distinct inbred line of tomato (*Lycopersicon esculentum*) having a high level resistance to Tomato Yellow Leaf Curl Virus.

BACKGROUND OF THE INVENTION

The goal of plant breeding is to develop new, unique and superior cultivars. Theoretically, a breeder can generate billions of different genetic combinations via crossing, selfing and selection. A breeder has no direct control at the cellular level. Therefore, two breeders will never develop the same line, or even very similar lines, having precisely the same traits. Descriptions of breeding methods that are commonly used for different traits and crops, as well as specifically for tomato, can be found in one of several reference books (e.g., Allard, R. W. (1960) *Principles of Plant Breeding*; Simmonds, N. W. (1979) *Principles of Crop Improvement*; Sneep, J. et al., (1979) *Tomato Breeding* (p. 135–171) in: *Breeding of Vegetable Crops*, Mark J. Basset, (1986, editor), *The Tomato crop: a scientific basis for improvement*, by Atherton, J. G. & J. Rudich, (1986, editors); *Plant Breeding Perspectives*; Fehr, (1987) *Principles of Cultivar Development—Theory and Technique*).

The method chosen for breeding or selection depends on the mode of plant reproduction, the heritability of the trait(s) being improved, and the cultivar (i.c. variety) used commercially (e.g. $F_1$ hybrid, or an open-pollinated variety). The complexity of the inheritance influences the choice of breeding method. One simple method of identifying a superior plant is to observe its performance relative to other experimental plants or to a widely grown standard cultivar, and to observe its performance in hybrid combinations with other plants. If single observations are inconclusive for establishing distinctness, observations in multiple locations and seasons provide a better estimate of its genetic worth. Proper testing and evaluation should detect any major faults and establish the level of superiority or improvement over current cultivars.

The development of commercial tomato hybrids requires the development of homozygous inbred parental lines. In breeding programs desirable traits from two or more germplasm sources or gene pools are combined to develop superior breeding lines. Desirable inbred or parent lines are developed by continuous selfing and selection of the best breeding lines, sometimes utilizing molecular markers to speed up the selection process.

Once the inbreds that give the best hybrid performance have been identified, the hybrid seed can be produced indefinitely, as long as the homogeneity and the homozygosity of the inbred parents is maintained. A single-cross hybrid is produced when two inbred lines are crossed to produce the $F_1$ progeny. Much of the hybrid vigor exhibited by $F_1$ hybrids is lost in the next generation ($F_2$). Consequently, seed harvested from hybrid varieties is not used for planting stock.

There are numerous steps involved in the breeding and development of any new and novel, desirable plant germplasm with superior combining ability. Plant breeding begins with the analysis and definition of problems and weaknesses of the current germplasm, the establishment of program goals, and definition of specific breeding objectives. The next step is selection of germplasm that possess the traits to meet the program goals and the definition of the best breeding method to reach those goals. The objective is to combine in a single hybrid variety an improved combination of desirable traits from the parental germplasm. Important characteristics may include higher yield, better flavor, improved color and field holding ability, resistance to diseases and insects, tolerance to drought and heat, along with characteristics related to hybrid seed yields to lower the cost of hybrid seed production.

Tomato is a very important crop in all continents of the world. Several plant species associated with the Solanum group have been familiar to mankind since ancient times, and are of great agricultural importance. Solanum species have a general adaptation to variable climatic growing conditions. Tomato (*Lycopersicon esculentum*) is adapted to warm summer growing conditions, but can also be grown in heated greenhouses under winter conditions. The introduction of hybrid cultivars in the 1950's provided a magnitude of benefits like increased yield, better holding ability, adaptation to expanded growing seasons through the use of protected cultivation and improved disease resistance, which resulted in large-scale production of tomato as a commercial crop. The goal in tomato breeding is to make continued improvements in hybrid tomato yields, in other horticultural characteristics, as well as in quality traits, in order to meet continuous demands for better tomato cultivars in different growing regions of the world.

Tomato (*Lycopersicon esculentum* L.) belongs to the Solaneaceous family. All varieties in the species esculentum are self-pollinating. Most other species in the genus Lycopersicon are cross-pollinating. Cross-pollination is affected by insect vectors, most commonly by the honey- or bumble-bees. Tomato, like most other Lycopersicon species, is highly variable. Variability in populations is desired for wide adaptation and survival.

SUMMARY OF THE INVENTION

The present invention relates to a new and distinct inbred fresh market tomato line, designated FDR 16-2045, having a high level of resistance to Tomato Yellow Leaf Curl Virus (TYLCV). Specifically, the present invention relates to inbred tomato seed designated FDR 16-2045 having ATCC Accession Number. The present invention further relates to a tomato plant grown from this tomato seed. Additionally, the present invention relates to pollen and ovules from this tomato plant and to an inbred tomato plant having all of the physiological and morphological characteristics of this tomato plant. Moreover, the present invention relates to a tomato plant regenerated from a tissue culture of tissue regenerated from this tomato plant.

The present invention also relates to a method of producing first generation ($F_1$) hybrid tomato seed. The method involves crossing a tomato plant produced by growing inbred tomato seed designated FDR 16-2045 having ATCC Accession No. with a second inbred line of tomato, and then harvesting the resulting $F_1$ seed. The tomato plant grown from the inbred tomato seed designated FDR 16-2045 having ATCC Accession No. may be used as either the female or male parent.

The present invention also relates to a first generation $F_1$ hybrid tomato plant that is produced by growing the hybrid tomato seed produced by the above-described method and to seed harvested on this hybrid tomato plant and plants grown from this seed.

The present invention also relates to tomato plants having within their pedigree tomato inbred line FDR 16-2045.

The present invention further relates to a method of producing a tomato variety FDR 16-2045-derived tomato plant. The first step of the method involves crossing tomato variety FDR 16-2045, representative seed of said tomato variety FDR 16-2045 having been deposited under ATCC Accession No. with a second tomato plant to yield progeny tomato seed. The second step of the method involves growing said progeny seed, under plant growth conditions, to yield a tomato variety FDR 16-2045-derived tomato plant. Optionally, the method further involves crossing said tomato variety FDR 16-2045-derived tomato plant with itself or another tomato plant to yield additional tomato variety FDR 16-2045-derived progeny tomato seed, growing said progeny tomato seed under plant growth conditions to yield additional tomato variety FDR 16-2045 derived tomato plants and repeating these crossing and growing steps from 0 to 7 or more times to generate further tomato variety FDR 16-2045-derived tomato plants.

Moreover, the present invention also relates to tomato variety FDR 16-2045-derived tomato plants, or plants thereof, produced by above-identified methods.

DETAILED DESCRIPTION OF THE INVENTION

The present invention relates to a new and distinct inbred fresh market tomato line, designated FDR 16-2045, having a high level of resistance to Tomato Yellow Leaf Curl Virus (hereinafter referred to as "TYLCV"). A high level of resistance to TYLCV is a very important trait, especially in the tomato growing areas around the Mediterranean basin and in the Middle East. This whitefly-transmitted geminivirus is spreading progressively and is a serious threat to other tomato areas around the world (see Czosnek, H. and H. Laterrot, (1997) "A worldwide survey of tomato yellow leaf curl viruses", *Arch. Virol.* 142: 1391–1406). The line FDR 16-2045 described herein can be used in hybrid combinations with other tomato lines to produce novel tomato varieties which are resistant to TYLCV.

Inbred tomato line FDR 16-2045 was developed from a cross made in 1992 with the wild tomato accession LA 1969 of Lycopersicon chilense. Line LA 1969 was obtained from Professor C. M. Rick of the "C. M. Rick Tomato Genetic Resources Center", Davis, Calif., and used as the source of TYLCV resistance as described in (Zamir, D., Michelson, I., Zakay, Y., Zeidan, N., Sarfatti, M., Eshed, Y., Harel, E. , Pleban, T., van-Oss, H., Rabinowitch, H. D., and Czosnek, H., (1994) "Mapping and introgression of a tomato yellow leaf curl tolerance gene, TY-1," *Theor. Appl. Genet.* 88:141–146).

This line LA 1969 was crossed to an anthocyanin-less variety Marmande Verte, which is a mutant of the publicly known variety Marmande listed in the Community Variety Catalogue of the European Community (Publication Journal of the EU, C167A). The resulting $F_1$ population was backcrossed to breeding line G 1001; backcross progeny lines were grown for observation and selection. Bulk pollen, sampled from *L. esculentum* breeding lines G122, G124, G125, G126, G127 and G128 was used to make backcross 2. *L. esculentum* breeding lines G132 and G130 were used to produce backcross 3 and backcross 4. G1001, G122, G124, G125, G126, G127, G128, G130 and G132 are proprietary breeding lines of Seminis Vegetable Seeds, Inc. (hereinafter "Seminis"), the assignee of the present invention.

The main traits selected for in each backcross progeny was a high level of resistance to TYLCV and resistance to other diseases such as tobacco mosaic virus, Verticillium race 0 and *Fusarium oxysporum* f. sp. lycopersici race 0 and 1 (European Union, Community Plant Variety Office, Technical Questionnaire TQ-EN-044), as well as commercially desirable traits such as, large fruit size, good fruit firmness and fruit color.

From 1994 to 1997, pedigree selection was applied for seven (7) subsequent generations. Finally, a plant identified as 97TK02/0604.01 was selected. Selfed seed from this line was sent to Seminis' Foundation Seed Department. The seed harvested as bulk from this line was saved as Foundation Seed and used as a parental line for the production of new experimental hybrid combinations. This seed was designated as FDR 16-2045.

Inbred line FDR 16-2045 has shown uniformity and stability for all traits. It has been self-pollinated and planted for a sufficient number of generations, with careful attention to uniformity of plant type to ensure homozygosity and phenotypic stability. No variant traits have been observed or are expected.

Definitions

In the examples described below, a number of terms are used herein. The terms are used to provide a clear understanding of the specifications and are used in accordance with the terminology defined in the UPOV Technical Guidelines for tomato (TG/4417), which is incorporated herein or as described otherwise.

Leaf shape—pinnate or bipinnate

Growth type—determinate or indeterminate

Peduncle abscission layer—absent or present (jointed) or absent (jointless)

Fruit size—very small, small, medium, large or very large

Fruit shape (longitudinal section)—flattened, slightly flattened, round, rectangular, cylindrical, heart-shaped, obovoid, ovoid, pear-shaped or strongly pear-shaped Fruit ribbing (at stem end)—absent, weak, medium, strong or very strong Fruit shoulder color—green or uniform color Time to maturity—early, medium or late

*Fusarium oxysporum* f. sp. lycopersici strains 0 and 1—resistance present (no symptoms) or resistance absent (susceptible, very severe growth retardation) Verticillium race 0—resistance present (no symptoms) or resistance absent (susceptible, very severe growth retardation)

Tobacco Mosaic Virus (TMV) strains 0, 1, 2 and 1—2—resistance present (no symptoms) or resistance absent (susceptible, very severe yellowing of the leaves)

*Meloidogyne incognita*—resistance is rated according to the root gall index. A variety is documented resistant when the mean gall index rating is smaller than or equal to 2.0, intermediate resistant when the gall index rating is between 2.1–3.5 and susceptible when the mean gall rating is >3.5.

Seedlings are tested for resistance to *Meloidogyne incognita* in trays composed of separate cells. One seedling is grown in each cell. Seedlings at emergence of the first true leaf are inoculated by adding 300 second-stage juvenile nematodes of *M. incognita* to each cell. Plants are incubated in the greenhouse at temperatures not exceeding 25° C. Rating is done 24 days after inoculation by pulling up each plant and inspecting the roots for the presence of galls. The following root gall index is used:

1= no galls present or 1–2 gall like swellings <1.0 mm in diameter.

3=3–10 galls present but smaller in size than those observed on the susceptible control.

5= roots are severely galled and deformed or if discrete galls are present, they are similar in size to those observed on the susceptible control.

Tomato Yellow Leaf Curl Virus (TYLCV)—resistance present, intermediate resistant or resistance absent (susceptible).

Resistance is defined as the ability of a plant variety to restrict the activities of a specific pathogen and/or restrict the symptoms and signs of a disease, when compared to susceptible varieties. Resistant varieties may exhibit some symptoms when specific pathogen or pest pressure is severe.

Varieties with an intermediate level of resistance to a specific pathogen may perform substantially better than susceptible varieties when moderate to severe pressure exists. These varieties may exhibit a greater range of symptoms compared to resistant varieties when grown under similar conditions of moderate to severe pathogen or pest pressure.

The following scale (0 to 4) was used to score for disease symptoms of TYLCV:

0: no symptoms
1: slight yellowing of leaves
2: clear yellowing symptoms on leaves with leaf curl
3: Stunted plants with severe symptoms of yellowing of leaves and leaf curl
4: Severely stunted plants with small yellowing curled leaves.

A variety is rated as resistant to TYLCV when the score is 0 –1, intermediate resistant when the score is 2 and susceptible when the score is either 3 or 4.

Plant and Fruit Characteristics

Line FDR 16-2045 is a vigorous plant that has a determinate growth type with bipinnate leaves. The peduncle abscission layer (pedicel) is present Cointed). Time of maturity is late in comparison to other varieties. It is an excellent parental line and provides for outstanding combining ability for plant type and fruit quality in cross combinations for determinate, as well as indeterminate hybrid combinations like 588656, 589956, 590556, 588956, 150477, 150440 (all determinate plant types) and 1652907 (indeterminate plant type).

The plant is resistant to the fungal diseases *Verticillium* race 0, *Fusarium oxysporum* f. sp. lycopersici races 0 and 1, to the virus diseases Tobacco Mosaic Virus (TMV) strain 0, strain 1, 2 and strain 1–2, and to Tomato Yellow Leaf Curl Virus (TYLCV) and it provides for an intermediate level of resistance to the nematode *Meloidogyne incognita*. The latter result was unexpected, as the Mi gene that provides resistance to *M. incognita* is dominant. Based on this knowledge, one would have expected FDR 16-2045 to be either resistant or susceptible.

Table 1 below, presents the results of the nematode test of tomato line FDR 16-2045, a susceptible control (Geneva 80, New York State Agricultural Experiment Station, Geneva, N.Y.), a resistant control (VFN 8, EU Community Catalogue), as well as of some hybrid combinations with line FDR 16-2045. Rating for resistance was done according to Seminis Disease Screening Protocols, as described before.

TABLE 1

| Entry | Resistance score 1998 | | | Resistance score 1999 | | | Remarks |
|---|---|---|---|---|---|---|---|
| | R 1 | R 3 | R 5 | R1 | R 3 | R 5 | |
| Geneva 80 | 0 | 0 | 16 | 0 | 0 | 24 | Susceptible control |
| VFN 8 | 17 | 0 | 0 | 24 | 0 | 0 | Resistant control |

TABLE 1-continued

| Entry | Resistance score 1998 | | | Resistance score 1999 | | | Remarks |
|---|---|---|---|---|---|---|---|
| | R 1 | R 3 | R 5 | R1 | R 3 | R 5 | |
| 588656 | 0 | 14 | 38 | 0 | 12 | 13 | Experimental hybrid |
| 589956 | 0 | 21 | 29 | 0 | 10 | 15 | Experimental hybrid |
| 588956 | 0 | 41 | 9 | 2 | 14 | 7 | Experimental hybrid |
| FDR 16-2045 | 0 | 42 | 10 | 5 | 21 | 3 | Experimental hybrid |

Table 2 below, provides the range of differences that exist for resistance to TYLCV, as rated on the basis of disease scores described before. This illustrates the resistance of FDR 16-2045, and of intermediate resistance and susceptibility in two (2) other Seminis proprietary breeding lines.

TABLE 2

| Breeding line | TYLCV rating | Remarks |
|---|---|---|
| FDR 16-2045 | 0 | Resistant |
| FDR 16-2051 | 1–2 | Intermediate resistant |
| 95C808 | 3–4 | Susceptible |

Breeding Nursery 98TK02; Fall 1998; Gazi Pasa, Turkey.

Fruit shape of fruit of FDR 16-2045 is slightly flattened with a uniform shoulder color (green shoulder absent). The fruit size is large with more than four locules, the fruit ribbing is medium at stem end and fruit color is turning red at maturity.

Table 3, provides the results of field observations on the resistance to TYLCV, fruit size and fruit shape in longitudinal section, fruit shoulder color, according to the UPOV Technical Guidelines for tomato and as described before. FDR 16-2045 has been used in hybrid combinations with other proprietary Seminis parental lines and has provided the experimental hybrids listed below in Table 3 and which are designated as 150440, 150477, 589956, 588956, 588656 and 590556. In addition, Table 3 contains field observations for several similar commercial tomato varieties that are sold in markets where TYLCV is a problem.

TABLE 3

| Hybrid | TYLCV rating | Fruit size | Fruit shape | Shoulder color | Remarks |
|---|---|---|---|---|---|
| 150440 | 0–1 | Large | Round | Absent | Experimental $F_1$ |
| 150477 | 0–1 | Very large | Slightly flattened | Absent | Experimental $F_1$ |
| 589956 | 0–1 | Medium | Round to slightly flattened | Present | Experimental $F_1$ |
| 588956 | 0–1 | Medium/large | Slightly flattened | Absent | Experimental $F_1$ |
| 588656 | 0–1 | Large | Slightly flattened | Absent | Experimental $F_1$ |
| 590556 | 0–1 | Large | Round to slightly flattened | Absent | Experimental $F_1$ |
| Petopride 2 | 3–4 | Small | Round | Present | Commercial $F_1$ Petoseed |
| Avinash 2 | 2–3 | Small | Round | Absent | Commercial $F_1$ Novartis |
| Asco FIFA | 0–2 | Medium | Round | Present | Commercial $F_1$ Novartis |

TABLE 3-continued

| Hybrid | TYLCV rating | Fruit size | Fruit shape | Shoulder color | Remarks |
|---|---|---|---|---|---|
| Asco Top | 0–2 | Small/medium | Round to slightly flattened | Absent | Commercial $F_1$ Novartis |
| Tyking | 0–1 | small/medium | flattened | Present | Commercial $F_1$ Royal Sluis |
| Al-Ramah | 0–2 | medium | round | Present | Commercial $F_1$ de Ruiter |
| Jackal | 1–3 | Small | Round to rectangular | Absent | Commercial $F_1$ Novartis |

Hybrid trial 98TJ02; Fall 1998 in Seminis Jordan Valley Station. In column 1, the hybrids (F1's) are listed. The other columns give the characteristics as defined in the definition section.

When the term inbred tomato plant is used in the context of the present invention, this also includes any single gene conversions of that inbred. The term single gene converted plant as used herein refers to those tomato plants which are developed by a plant breeding technique called backcrossing wherein essentially all of the desired morphological and physiological characteristics of an inbred are recovered in addition to the single gene transferred into the inbred via the backcrossing technique.

Backcrossing methods can be used with the present invention to improve or introduce a characteristic into the inbred. The term backcrossing as used herein refers to the repeated crossing of a hybrid progeny back to one of the parental tomato plants for that inbred. The parental tomato plant which contributes the gene for the desired characteristic is termed the nonrecurrent or donor parent. This terminology refers to the fact that the nonrecurrent parent is used one time in the backcross protocol and therefore does not recur. The parental tomato plant to which the gene or genes from the nonrecurrent parent are transferred is known as the recurrent parent as it is used for several rounds in the backcrossing protocol. In a typical backcross protocol, the original inbred of interest (recurrent parent) is crossed to a second inbred (nonrecurrent parent) that carries the single gene of interest to be transferred. The resulting progeny from this cross are then crossed again to the recurrent parent and the process is repeated until a tomato plant is obtained wherein essentially all of the desired morphological and physiological characteristics of the recurrent parent are recovered in the converted plant, in addition to the single transferred gene from the nonrecurrent parent.

The present invention also contemplates a tomato plant regenerated from a tissue culture of an inbred (e.g., FDR 16-2045) or hybrid plant of the present invention. As is well known in the art, tissue culture of tomato can be used for the in vitro regeneration of a tomato plant. Kartha, K. K., Gamborg, O. L., Shyluk, J. P., and Constabel, F., Morphogenetic investigations on in vitro leaf cultures of tomato (Lycopersicon esculentum Mill. cv. Starfire) and high frequency plant regeneration, Z. Pflanzenphysiol., 77, 292, 1976.

Deposit Information

A deposit of the Seminis Vegetable Seeds proprietary inbred tomato line FDR 16-2045 disclosed above and recited in the appended claims has been made with the American Type Culture Collection (ATCC), 10801 University Boulevard, Manassas, Virginia 20110. The date of deposit was Apr. 5, 2002. The deposit of 2,500 seeds were taken from the same deposit maintained by Seminis Vegetable Seeds since prior to the filing date of this application. All restrictions upon the deposit have been removed, and the deposit is intended to meet all of the requirements of 37 C.F.R. §1.801–1.809. The ATCC accession number is PTA-4208. The deposit will be maintained in the depository for a period of 30 years, or 5 years after the last request, or for the effective life of the patent, whichever is longer, and will be replaced as necessary during that period.

Although the foregoing invention has been described in some detail by way of illustration and example for purposes of clarity and understanding, it will be obvious that certain changes and modifications may be practiced within the scope of the invention, as limited only by the scope of the appended claims.

What is claimed is:

1. An inbred tomato seed designated FDR 16-2045, a sample of said seed having been deposited under American Type Culture Collection Accession No. PTA-4208.

2. A tomato plant, or parts thereof, produced by growing the seed of claim 1.

3. Pollen of the plant of claim 2.

4. An ovule of the plant of claim 2.

5. A tomato plant, or parts thereof, having all of the physiological and morphological characteristics of the tomato plant of claim 2.

6. The tomato plant of claim 2, wherein said plant is male sterile.

7. A tissue culture of regenerable cells of a tomato plant of inbred line FDR 16-2045, wherein the tissue regenerates plants capable of expressing all the morphological and physiological characteristics of the inbred line FDR 16-2045.

8. A tissue culture according to claim 7, comprising cells or protoplasts from a tissue selected from the group consisting of leaves, pollen, embryos, roots, root tips, anthers, flowers, fruit, and seeds.

9. A tomato plant regenerated from the tissue culture of claim 7, capable of expressing all the morphological and physiological characteristics of inbred line FDR 16-2045.

10. A method for producing a hybrid tomato seed comprising crossing a first inbred parent tomato plant with a second inbred parent tomato plant and harvesting the resultant hybrid tomato seed, wherein said first or second parent tomato plant is the tomato plant of claim 2.

11. A hybrid tomato seed produced by the method of claim 10.

12. A hybrid tomato plant, or parts thereof, produced by growing said hybrid tomato seed of claim 11.

13. Tomato seed produced by growing said hybrid tomato plant of claim 12.

14. A tomato plant, or parts thereof, produced from seed of claim 13.

15. A method for producing a hybrid tomato seed comprising crossing an inbred plant according to claim 2 with another, different tomato plant and harvesting the resultant hybrid tomato seed.

16. A hybrid tomato seed produced by the method of claim 15.

17. A hybrid tomato plant, or its parts, produced by growing said hybrid tomato seed of claim 16.

18. Tomato seed produced from said hybrid tomato plant of claim 17.

19. A tomato plant, or its parts, produced from the tomato seed of claim 18.

20. A method for producing a FDR 16-2045-derived tomato plant, comprising:

a) crossing inbred tomato line FDR 16-2045, a sample of seed of said line having been deposited under American Type Culture Collection accession number, with a second tomato plant to yield progeny tomato seed;

b) growing said progeny tomato seed, under plant growth conditions, to yield said FDR 16-2045-derived tomato plant.

21. The method of claim 20, further comprising:

c) crossing said FDR 16-2045-derived tomato plant with itself or another tomato plant to yield additional FDR 16-2045-derived progeny tomato seed;

d) growing said progeny tomato seed of step (c) under plant growth conditions, to yield additional FDR 16-2045-derived tomato plants;

e) repeating the crossing and growing steps of (c) and (d) from 0 to 7 times to generate further FDR 16-2045-derived tomato plants.

22. The method of claim 20, still further comprising utilizing plant tissue culture methods to derive progeny of said FDR 16-2045-derived tomato plant.

23. The tomato plant, or parts thereof, of claim 2, wherein the plant or parts thereof have been transformed so that its genetic material contains one or more transgenes operably linked to one or more regulatory elements.

24. A method for producing a tomato plant that contains in its genetic material one or more transgenes, comprising crossing the tomato plant of claim 23 with either a second plant of another tomato line, or a non-transformed tomato plant of the line FDR 16-2045, so that the genetic material of the progeny that result from the cross contains the transgene(s) operably linked to a regulatory element.

25. Tomato plants, or parts thereof, produced by the method of claim 24.

26. The tomato plant of claim 5, further comprising a single gene conversion.

27. The tomato plant of claim 26, further comprising a cytoplasmic factor conferring male sterility.

28. The tomato plant of claim 26, wherein said single gene is selected from the group consisting of: a transgenic gene, a dominant allele, and a recessive allele.

29. The tomato plant of claim 26, wherein said single gene confers a characteristic selected from the group consisting of: herbicide resistance, insect resistance, resistance to bacterial, fungal, or viral disease, male sterility, and improved nutritional quality.

* * * * *